(12) United States Patent
Bhirud et al.

(10) Patent No.: US 12,378,217 B2
(45) Date of Patent: Aug. 5, 2025

(54) PROCESS FOR THE PREPARATION OF LASMIDITAN

(71) Applicant: Alivus Life Sciences Limited, Solapur (IN)

(72) Inventors: Shekhar Bhaskar Bhirud, Mumbai (IN); Samir Naik, Thane (IN); Shafakat Ali Nasir Ali, Thane (IN); Pramod Vitthal Patil, Panvel (IN); Deepak Baviskar, Mumbai (IN); Mahendra Ramesh Patil, Jalgaon (IN); Venkata Raghavendra Acharyulu Palle, Pune (IN)

(73) Assignee: Alivus Life Sciences Limited, Solapur (IN)

( * ) Notice: Subject to any disclaimer, the term of this patent is extended or adjusted under 35 U.S.C. 154(b) by 508 days.

(21) Appl. No.: 17/795,641

(22) PCT Filed: Jan. 27, 2021

(86) PCT No.: PCT/IB2021/050603
§ 371 (c)(1),
(2) Date: Jul. 27, 2022

(87) PCT Pub. No.: WO2021/152462
PCT Pub. Date: Aug. 5, 2021

(65) Prior Publication Data
US 2023/0095474 A1    Mar. 30, 2023

(30) Foreign Application Priority Data
Jan. 31, 2020  (IN) .............................. 202021004381

(51) Int. Cl.
*C07D 401/06*  (2006.01)
*C07D 213/81*  (2006.01)

(52) U.S. Cl.
CPC ......... *C07D 401/06* (2013.01); *C07D 213/81* (2013.01)

(58) Field of Classification Search
CPC ........................... C07D 401/06; C07D 213/81
See application file for complete search history.

(56) References Cited

U.S. PATENT DOCUMENTS

| 10,669,256 | B2 | 6/2020 | Sheng et al. | |
| 2013/0072524 | A1* | 3/2013 | Carniaux | C07D 401/06 546/194 |
| 2019/0233393 | A1* | 8/2019 | Sheng | C07D 401/06 |

FOREIGN PATENT DOCUMENTS

WO       2018010345 A1    1/2018

* cited by examiner

*Primary Examiner* — D Margaret M Seaman
(74) *Attorney, Agent, or Firm* — Michael E. Carmen

(57) ABSTRACT

The present invention relates to a process for the preparation of lasmiditan, a compound of formula I, or pharmaceutically acceptable salts thereof, the process comprising reacting a compound of formula IV with morpholine to obtain a compound of formula II, reacting the of formula III with a compound of formula IIA to obtain lasmiditan or salt thereof.

11 Claims, 1 Drawing Sheet

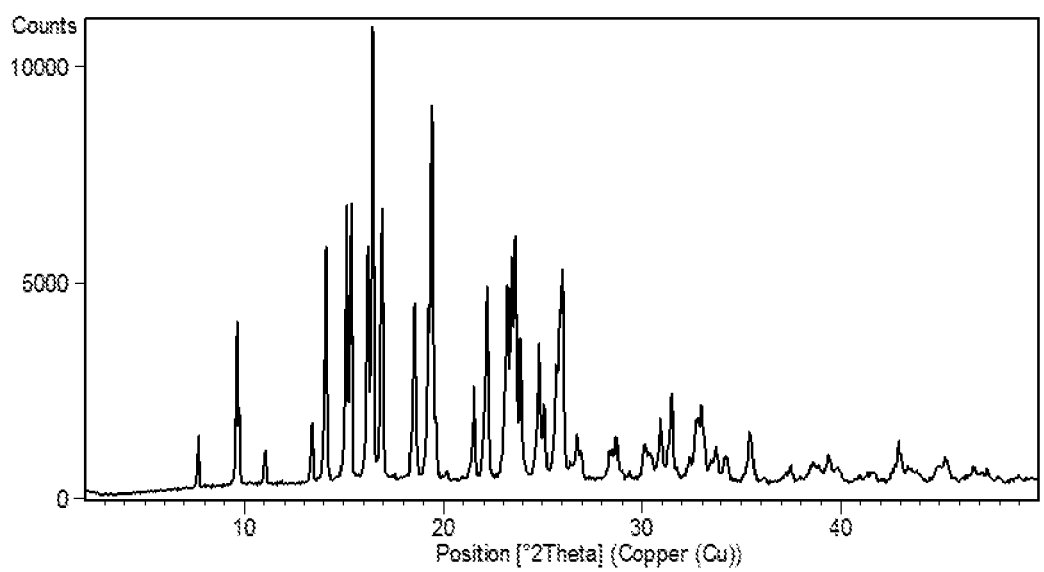

PROCESS FOR THE PREPARATION OF LASMIDITAN

PRIORITY

This application claims priority under 35 U.S.C. § 371 to International Application No. PCT/IB2021/050603, filed Jan. 27, 2021, which claims the benefit of Indian Provisional Application No. 202021004381, filed on Jan. 31, 2020, and entitled "PROCESS FOR PREPARATION OF LASMIDITAN", the contents of which are incorporated herein by reference.

BACKGROUND OF THE INVENTION

Technical Field

The present invention relates to a process for the preparation of lasmiditan and salts thereof.

Description of the Related Art

Lasmiditan, is a serotonin (5-HT) 1F receptor agonist, also known as 2,4,6-trifluoro-N-[6-(1-methylpiperidine-4-carbonyl)pyridine-2-yl]benzamide, represented by the structure of formula I.

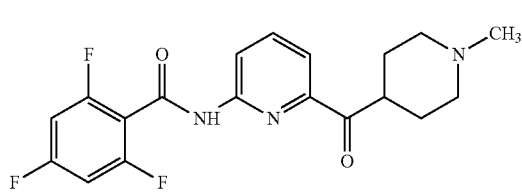

Lasmiditan hemisuccinate, a compound of formula IA marketed as Reyvow® is a tablet available in multiple strengths for oral administration and is indicated for the acute treatment of migraine with or without aura in adults.

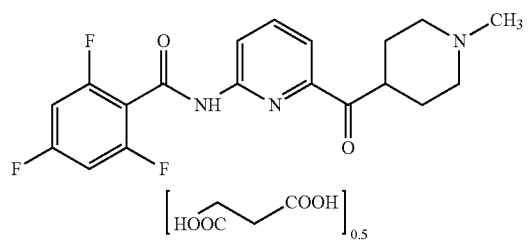

SUMMARY OF THE INVENTION

In one embodiment, the present invention provides a process for lasmiditan, a compound of formula I, or pharmaceutically acceptable salts thereof,

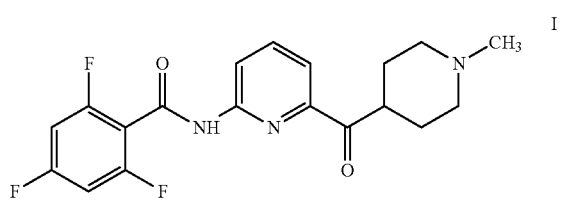 [SMILES: CN1CCC(C(=O)c2cccc(NC(=O)c3c(F)cc(F)cc3F)n2)CC1]

the process comprising:

a) reacting a compound of formula III with a compound of formula IIA,

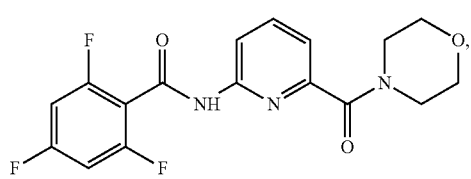

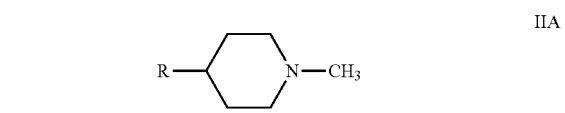

wherein R is MgX, Li, ZnX, Sn $(C_1-C_6$ alkyl$)_3$; X is selected from the group consisting of Br, Cl, I; to obtain lasmiditan, the compound of formula I; and b) optionally, converting lasmiditan, the compound of formula I to a pharmaceutically acceptable salt.

In another embodiment, the present invention provides a compound of formula III,

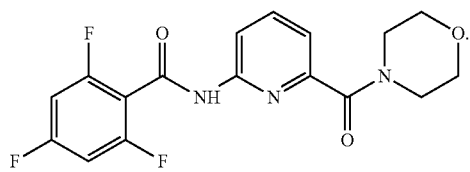

In another embodiment, the present invention provides use of the compound of formula III,

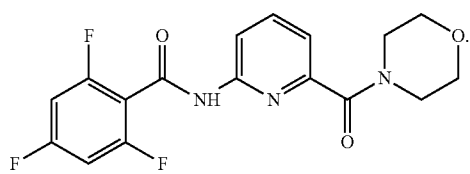

In another embodiment, the present invention provides use of the compound of formula III,

[Structure III shown: 2,4,6-trifluorobenzamide linked via NH to a pyridine bearing a morpholine carbonyl group]

in the preparation of lasmiditan, the compound of formula I or pharmaceutically acceptable salts thereof.

BRIEF DESCRIPTION OF THE DRAWINGS

FIG. 1 is a characteristic XRPD diagram of lasmiditan hemisuccinate as obtained in example 10.

DETAILED DESCRIPTION OF THE INVENTION

In one embodiment, the present invention provides a process for lasmiditan, a compound of formula I, or pharmaceutically acceptable salts thereof,

[Structure I: lasmiditan — 2,4,6-trifluorobenzamide-NH-pyridine-C(O)-(1-methylpiperidin-4-yl)]

the process comprising:
a) reacting a compound of formula III with a compound of formula IIA,

[Structure III shown again]

[Structure IIA: R—(1-methylpiperidin-4-yl)]

wherein R is MgX, Li, ZnX, Sn(C$_1$-C$_6$ alkyl)$_3$; X is selected from the group consisting of Br, Cl, I; to obtain lasmiditan, the compound of formula I; and
b) optionally, converting lasmiditan, the compound of formula I to a pharmaceutically acceptable salt.

In one embodiment, the present invention provides a process for the preparation of lasmiditan, the compound of formula I, the process comprising reacting the compound of formula III with the compound of formula IIA, wherein R is MgX, Li, ZnX, Sn(C1-C6 alkyl)3; X is selected from the group consisting of Br, Cl, I; to obtain lasmiditan, the compound of formula I.

In one embodiment, the compound of formula III, is reacted with the compound of formula IIA, wherein R is MgX and X is Cl, Br or I, in step 'a' to obtain lasmiditan, the compound of formula I.

[Structure III shown again]

[Structure IIA: R—(1-methylpiperidin-4-yl)—N—CH$_3$]

In one embodiment, the compound of formula III is reacted with the compound of formula IIA, wherein R is MgX and X is Cl, the compound of formula IIA.

In one embodiment, the reaction of the compound of formula III with the compound of formula IIA, wherein R is MgX and X is Cl, Br or I, may be carried out at the temperature of about −30° C. to about 30° C.

In one embodiment, the reaction of the compound of formula III with the compound of formula IIA, wherein R is MgX and X is Cl, Br or I, may be carried out at the temperature of about −20° C. to about 10° C.

In one embodiment, the reaction of the compound of formula III with the compound of formula IIA, wherein R is MgX and X is Cl, Br or I, may be carried out in a solvent.

In one embodiment, the solvent may be selected from the group consisting of water, tetrahydrofuran, diethyl ether, MTBE and the like.

In one embodiment, the compound of formula IIA may be prepared first and then reacted with the compound of formula III.

In one embodiment, the compound of formula IIA may be formed in situ, wherein the compound of formula III is present, to which the compound of formula VA and magnesium is added.

In one embodiment, the compound of formula IIA, wherein R is MgX and X is Cl, Br or I, may be prepared by the process comprising reacting the compound of formula VA wherein X is Cl, Br or I; with magnesium.

[Structure VA: X—(1-methylpiperidin-4-yl)—N—CH$_3$]

In one embodiment, the compound of formula III is reacted with the compound of formula VA such that, the compound of formula IIA is formed in situ.

In one embodiment, the compound of I is prepared by reacting the compound of formula III with the compound of formula VA wherein X is Cl, Br or I.

In one embodiment, the compound of I is prepared by reacting the compound of formula III with the compound of formula VA wherein X is Cl, Br or I; in the presence of Grignard reagent or turbo Grignard reagent.

In one embodiment, the Grignard reagent is selected from the group consisting of methyl magnesium halide, ethyl magnesium halide, propyl magnesium halide, isopropyl magnesium halide, butyl magnesium halide, t-butyl magnesium halide and the like In one embodiment, the Grignard reagent is alkyl magnesium halide.

In one embodiment, lasmiditan, the compound of formula I is prepared by reacting a compound of formula III with a compound of formula VA wherein X is Cl, Br or I.

In one embodiment, lasmiditan, the compound of formula I is prepared by reacting a compound of formula III with a compound of formula VA, wherein X is Cl, Br or I, in the presence of a base.

In one embodiment, the base may be selected from the group consisting of alkyl lithium, Grignard reagent, naphthalene, zinc chloride, calcium hydroxide, t-butoxide, lithium halide, tributyl tin chloride and the like.

In one embodiment, the base is butyl lithium.

In one embodiment, the present invention provides a process wherein lasmiditan, the compound of formula I, is obtained in crystalline form.

In one embodiment, in step 'b' of the above process, lasmiditan, a compound of formula I, may be converted to pharmaceutically acceptable salt.

In one embodiment, lasmiditan, the compound of formula I, may be converted to hydrochloride salt.

In one embodiment, lasmiditan, the compound of formula I, may be converted to hemisuccinate salt, the compound of formula IA.

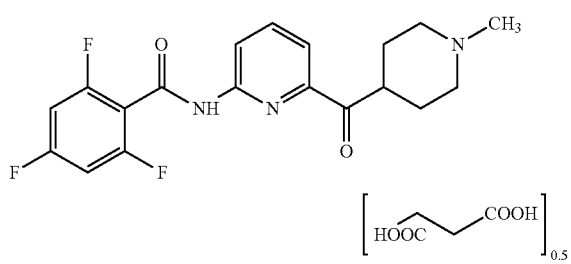

In one embodiment, lasmiditan hemisuccinate, the compound of formula IA, is prepared by reacting lasmiditan, the compound of formula I with succinic acid.

In one embodiment, lasmiditan hemisuccinate, the compound of formula IA, is prepared by reacting lasmiditan, the compound of formula I with succinic acid in a suitable solvent.

The solvent includes but is not limited to esters such as methyl acetate, ethyl acetate, isopropyl acetate, t-butyl acetate, and the like; hydrocarbons such as toluene, xylene, heptane, hexane and the like; ethers such as diethyl ether, diisopropyl ether, methyl t-butyl ether, tetrahydrofuran and the like; ketones such as acetone, methyl isobutyl ketone and the like; alcohols such as methanol, ethanol, n-propyl alcohol, isopropyl alcohol, n-butanol and the like; haloalkane such as dichloromethane, chloroform, ethylene dichloride and the like; diemthyl sulfoxide, diemthyl acetamide, water or mixture thereof.

In one embodiment, lasmiditan or salt thereof are purified by any method known in the art. The method, may involve any of the techniques, known in the art, including recrystallization, column chromatography, extraction, filtration, slurrying in solvent, precipitation from a solvent, and the like.

In one embodiment, lasmiditan or salt thereof are purified by dissolving in a solvent system and recrystallizing.

In one embodiment, lasmiditan or salt thereof are purified by dissolving in a solvent system and adding an anti-solvent.

In one embodiment, lasmiditan or salt thereof is purified by recrystallization from water.

In one embodiment, lasmiditan or salt thereof is purified by recrystallization from IPA.

In one embodiment, the present invention provides a process wherein, lasmiditan, the compound of formula I is obtained in a purity of ≥99%, as determined by HPLC.

In one embodiment, the present invention provides a process wherein, lasmiditan hemisuccinate, the compound of formula IA is obtained in a purity of ≥99%, as determined by HPLC.

In one embodiment, the present invention provides a compound of formula III,

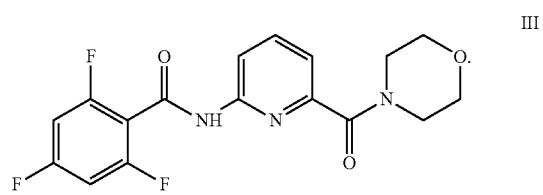 [SMILES: O=C(Nc1cccc(C(=O)N2CCOCC2)n1)c1c(F)cc(F)cc1F]

In one embodiment, the present invention provides a compound of formula III,

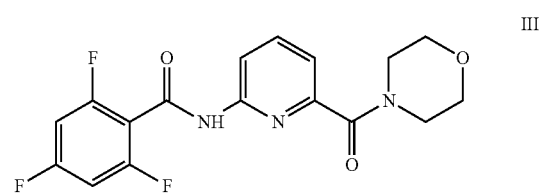 [SMILES: O=C(Nc1cccc(C(=O)N2CCOCC2)n1)c1c(F)cc(F)cc1F]

characterized by 1H NMR having characteristic peaks at δ (ppm): 3.35, 3.55, 3.64, 7.36, 8.0, 8.2.

In one embodiment, the compound of formula III is prepared by a process comprising reacting a compound of formula IV,

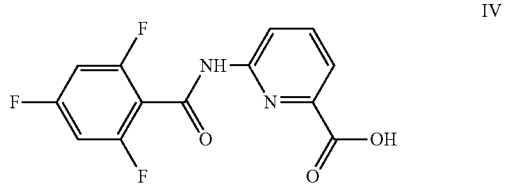 [SMILES: O=C(O)c1cccc(NC(=O)c2c(F)cc(F)cc2F)n1]

with morpholine to obtain the compound of formula III.

In one embodiment, the reaction of the compound of formula IV with morpholine may be carried out in the presence of coupling reagent.

In one embodiment, the coupling reagent may be selected from the group consisting of carbodiimides, 1-hydroxybenzotriazole phosphonium and uranium salts, 1-hydoxy-7-azabenzotriazole phosphonium and uranium salts, sulfinyl halide and phosphorus halide, carbonyl diimidazole.

In one embodiment, the carbodiimide coupling reagent may be selected from the group consisting of N,N'-dialkylcarbodiimides such as N,N'-dicyclohexyl carbodiimide (DCC) or diisopropylcarbodiimide (DIPC), 1-ethyl-3-(3-dimethylamino propyl)-carbodiimide (EDC) and the like.

In one embodiment, the 1-hydroxybenzotriazole phosphonium and uranium salts may be selected from the group consisting of benzotriazol-1-yl-N-oxy-tris(dimethylamino)

phosphonium hexafluoro-phosphate (BOP), benzotriazol-1-yl-N-oxy-tris(pyrrolidino)phosphonium hexafluorophosphate (PyBOP), N,N-[(1H-benzotriazol-1-yl)(dimethylamino)methylene]-N-methylmethanaminium hexafluorophosphate N-oxide (HBTU), N-[(1H-benzotriazol-1-yl)(dimethylamino) methylene]-N-methylmethanaminium tetrafluoroborate N-oxide (TBTU), N-[(1H-6-chlorobenzotriazol-1-yl)(dimethylamino)-methylene]-N-methylmethanaminium hexafluorophosphate N-oxide (HCTU), N-[(1H-6-chlorobenzotriazol-1-yl) (dimethylamino)methylene]-N-methylmethanaminium tetrafluoroborate N-oxide (TCTU), hydroxybenzotriazole (HOBT) and the like.

In one embodiment, the 1-hydoxy-7-azabenzotriazole phosphonium and uranium salts may be selected from the group consisting of, 7-azabenzotriazol-1-yl-N-oxytris(pyrrolidino)phosphoniumhexafluorophosphate (PyAOP), N-[(dimethylamino)-1H-1,2,3-triazolo[4,5-b]pyridino-aylmethylene]-N-methylmethanaminiumhexafluoro phosphate (HATU) and the like.

In one embodiment, sulfinyl halide may be selected from the group consisting of thionyl chloride and the like.

In one embodiment, phosphorus halide may be selected from the group consisting of phosphorus oxychloride, phosphorus trichloride, phosphorus pentachloride and the like.

In one embodiment, the reaction of the compound of formula IV with morpholine may be carried out in presence of a base.

In one embodiment, the base may be selected from the group consisting of organic base, inorganic base and mixtures thereof.

In one embodiment, the organic base may be selected from the group consisting of amines, organolithiums, tetraalkylammonium hydroxides, phosphonium hydroxides and the like.

In one embodiment, the amine may be selected from the group consisting of cyclic aliphatic amine, trialkyl amines, heterocyclic amine, C1-C6 aliphatic amine, C6-C12 aryl alkyl amines, C6-C12 aryl amines and the like.

In one embodiment, the cyclicaliphatic amine may be selected from the group consisting of cyclohexyl amine, dicyclohexyl amine, piperidine, piperazine and the like. In one embodiment, the trialkyl amine may be selected from the group consisting of triethylamine, diisoporpylethylamine (DIPEA) and the like.

In one embodiment, the heterocyclic amine may be selected from the group consisting of 1, 8-diazabicyclo[5.4.0]undec-7-ene (DBU), 1,5-diazabicyclo[4.3.0]non-5 5-ene (DBN), 1,4-diazabicyclo[2.2.2]octane (Dabco) pyridine, pyrimidine, 4-(dimethylamino)pyridine (DMAP) and the like.

In one embodiment, the C1-C6 aliphatic amine may be selected from the group consisting of methyl amine, propyl amine, n-butylamine and the like.

In one embodiment, C6-C12 aryl alkylamine may be selected from the group consisting of benzyl amine, phenyl ethyl amine, and the like.

In one embodiment, the C6-C12 aryl amine may be selected from the group consisting of aniline and the like.

In one embodiment, the organolithium may be selected from the group consisting of methyllithium, n-butyllihtium, t-butyllithium and the like.

In one embodiment, the tetraalkylammonium hydroxide may be selected from the group consisting of tetrabutylammonium hydroxide (TBAH), tetramethylammonium hydroxide and the like.

In one embodiment, the phosphonium hydroxide may be selected from the group consisting of tetrabutyl phosphonium hydroxide and the like.

In one embodiment, the inorganic base may be selected from the group consisting of metal carbonate, metal bicarbonate, metal hydroxide and metal alkoxides wherein the metal is selected from the group consisting of sodium, potassium, lithium, calcium, cesium or magnesium.

In one embodiment, the reaction of the compound of formula IV with morpholine is carried out in a solvent.

In one embodiment, the solvent may be selected from the group consisting of C1-C6 halogenated hydrocarbon, C3-C8 ethers, C3-C8 hydrocarbons, C3-C8 esters, nitriles, amides, sulfoxides and mixtures thereof.

In one embodiment, the solvent may be selected from the group consisting of halogenated hydrocarbons such as dichloromethane, dichloroethane, chloroform, and the like; ethers such as dimethyl ether, diethyl ether, diisopropyl ether, tert-butyl methyl ether, dibutyl ether, dimethoxyethane, diethoxyethane, tetrahydrofuran, dioxane and the like; hydrocarbons such as toluene, xylene, chlorobenzene, heptane, hexane, cyclohexane and the like; esters such as methyl acetate, ethyl acetate, n-propyl acetate, tert-butyl acetate and the like; nitriles such as acetonitrile, benzonitrile and the like; amides such as dimethylformamide, dimethylacetamide and the like; sulfoxides such as dimethyl sulfoxide; and mixtures thereof.

In one embodiment, the present invention provides a use of the compound of formula III, in the preparation of lasmiditan, the compound of formula I, or pharmaceutically acceptable salts thereof.

In one embodiment, the present invention provides a process for lasmiditan, a compound of formula I, or pharmaceutically acceptable salts thereof,

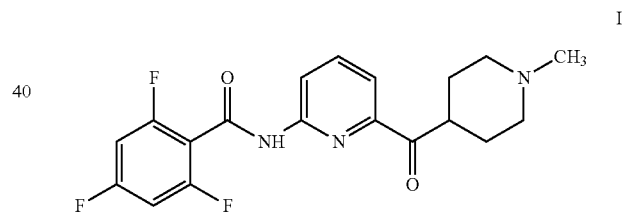

I the process comprising reacting the compound of formula IIIA with a compound of formula IIA,

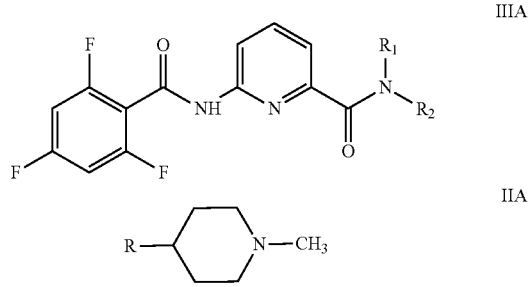

IIIA

IIA wherein, R1 and R2 are independently selected from the group consisting of C1-C6 alkyl, C6-C8 aryl, C6-C8 arylC1-C6alkyl and C1-C6alkylC6-C8aryl, C3-C6 cycloalkyl, C3-C6 cycloheteroalkyl or R1 and R2 together with the nitrogen to which they are attached form C3-C8 heterocyclic ring with one or more heteroatoms selected from O, S or N and R is MgX, Li, ZnX, Sn(C1-C6 alkyl)3; X is selected from the group consisting of Br, Cl, I; to obtain lasmiditan, the compound of formula I; and b) optionally, converting lasmiditan, the compound of formula I to a pharmaceutically acceptable salt.

In one embodiment, the present invention provides a process for lasmiditan, a compound of formula I, or pharmaceutically acceptable salts thereof,

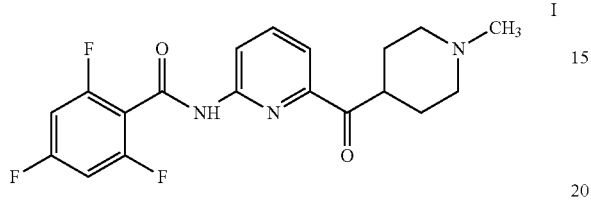

I the process comprising reacting the compound of formula IIIA with a compound of formula IIA,

IIIA

IIA wherein, R1 and R2 together with the nitrogen to which they are attached form a C3-C8 heterocyclic ring with one or more heteroatoms selected from O, S or N and R is MgX, Li, ZnX, Sn($C_1$-$C_6$ alkyl)$_3$; X is selected from the group consisting of Br, Cl, I; to obtain lasmiditan, the compound of formula I; and b) optionally, converting lasmiditan, the compound of formula I to a pharmaceutically acceptable salt.

The term "C1-C6 alkyl" means alkyl groups having 1 to 6 carbon atoms and includes groups such as methyl, ethyl, n-propyl, isopropyl, n-butyl, isobutyl, t-butyl, n-pentyl.

The term "C6-C12 aryl" means aryl groups having 6 to 12 carbon atoms and include groups such as phenyl, naphthyl.

The term "C6-C8arylC1-C6alkyl" means aryl groups substituted with alkyl groups and includes groups such as benzyl, phenylethyl, tolulyl.

The term "C1-C6alkylC6-C8aryl" means alkyl groups substituted with aryl group and include groups such as methylphenyl, ethylphenyl.

The term "C3-C6 cycloalkyl" means aliphatic cyclic groups and includes groups such as cyclpropyl, cyclobutyl, cyclohexane.

The term "C3-C6 cycloheteroalkyl" means aliphatic cyclic groups with 1-3 heteroatom in the ring selected from S, O or N and includes groups such as pyrrolidinyl, piepridinyl, morpholinyl.

In one embodiment, the present invention provides lasmiditan free of any of the below listed impurities A-H.

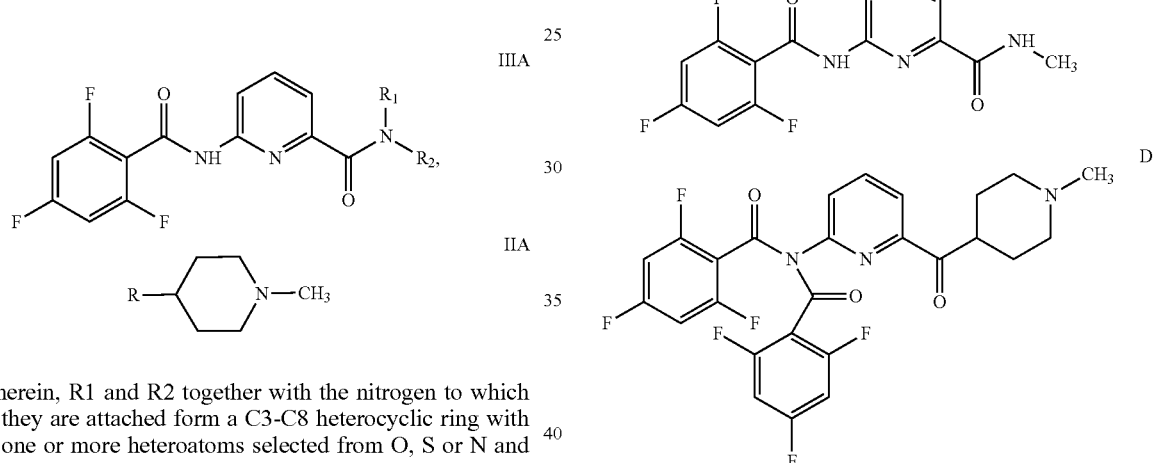

A

B

C

D

E

F

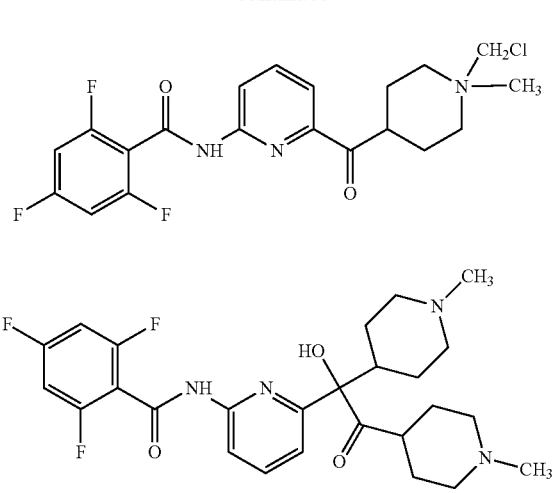

In one embodiment, the present invention provides pharmaceutical compositions comprising lasmiditan or salt thereof obtained by the processes described herein, having a D90 particle size of less than about 250 microns, preferably less than about 150 microns, more preferably less than about 50 microns, still more preferably less than about 20 microns, still more preferably less than about 15 microns and most preferably less than about 10 microns.

In one embodiment, the present invention provides pharmaceutical compositions comprising lasmiditan or salt thereof obtained by the processes herein described, having a D50 particle size of less than about 250 microns, preferably less than about 150 microns, more preferably less than about 50 microns, still more preferably less than about 20 microns, still more preferably less than about 15 microns and most preferably less than about 10 microns.

The particle size disclosed here can be obtained by, for example, any milling, grinding, micronizing or other particle size reduction method known in the art to bring the solid state lasmiditan or salt thereof into any of the foregoing desired particle size range.

XRD Method: X-ray powder diffraction profiles were obtained using an X-ray diffractometer (Philips X'Pert Pro, PANalytical). The measurements were carried out with a Pre FIX module programmable divergence slit and anti-scatter Slit (Offset 0.00°); target, Cu filter, Ni detector, X'Celerator; Scanning Mode; Active length (2θ)=2.122°; generator 45KV; tube current 40 mAmp. Start angle: 2°; End angle: 50° and with a time per step, 50 seconds.

HPLC Method: High performance liquid chromatography (HPLC) was performed with the conditions described below for detecting purity: Column: Inertsil ODS 3V, 250×4.6 mm, 5μ, Column temperature:40° C., Mobile phase: A: Buffer: 1.0 mL of Perchloric acid and 0.5 g of Pentane sulfonic acid sodium salt into 1000 ml water, mix well (100%) Mobile Phase B: Acetonitrile (100%), Diluent:Water:ACN (50:50, v/v); Flow Rate: 1.0 mL/min, Detection wavelength: UV 225 nm, Injection volume: 10 μL.

The examples that follow are provided to enable one skilled in the art to practice the invention and are merely illustrative of the invention. The examples should not be read as limiting the scope of the invention as defined in the features and advantages.

EXAMPLES

Example 1

Preparation of Compound of Formula III

To a mixture of 6-[(2,4,6-trifluorobenzoyl)amino]pyridine-2-carboxylic acid (IV, 20 g) in ethyl acetate (150 ml), N,N'-dicyclohexyl carbodiimide (DCC, 15.3 g), hydroxybenztriazole (HOBT, 11.0 g), N-methylmorpholine (10.2 g) and morpholine (7.0 g) were added and stirred at about 25° C. to about 30° C. for about 4 h to about 5 h. The progress of reaction was monitored using TLC/HPLC. After the completion of reaction, the reaction mass was cooled at about 0° C. to about 5° C., filtered through Hyflo bed and washed with ethyl acetate. The filtrate was washed with water, aq sodium carbonate solution and aqueous sodium chloride solution. The organic layer was separated and concentrated under vacuum at about 45° C. to about 50° C. The residue obtained was crystallized from diisopropyl ether to obtain compound III. Yield: 20.5 g (83%). $^1$H NMR (DMSO) ppm 3.35(t, 2H) 3.55(t, 2H) 3.64(t, 4H) 7.36(m, 3H) 8.0(s, 1H) 8.2(s, 1H); Mass: m/z=366.13 (M+1).

Example 2

Preparation of Compound of Formula III

To a stirred solution of 6-[(2,4,6-trifluorobenzoyl)amino]pyridine-2-carboxylic acid (IV, 5 g) in dimethyl formamide (25 ml), DCC (3.8 g), HOBT (2.7 g), N-methylmorpholine (2.6 g), morpholine (1.8 g) were added and stirred at about 25° C. to about 30° C. for about 4 h to about 5 h. The progress of reaction was monitored using TLC/HPLC. After the completion of reaction, the reaction mass was filtered through Hyflo bed and washed with DMF. Aqueous sodium carbonate solution was added to the filtrate, stirred at about 25° C. to about 30° C. and filtered to obtain the compound of formula III. Yield: 4.8 g (78.14%).

Example 3

Preparation of Compound of Formula III

To a stirred solution of 6-[(2,4,6-trifluorobenzoyl)amino] pyridine-2-carboxylic acid (IV, 5 g), in THF (50 ml) & dimethyl formamide (0.2 ml), oxalyl chloride (2.9 ml) was added and stirred at about 25° C. to about 30° C. for about 1 h. The reaction mass was further stirred at about 40° C. to about 45° C. for about 2 h to about 3 h. After the completion of reaction, the reaction mass was concentrated under vacuum at about 40° C. The residue was charged in THF, cooled to about 0° C. to about 5° C., solution of N-methyl morpholine (3.8 ml), morpholine (1.9 ml) in THF were added and stirred for about 30 min. The reaction mass was further stirred at about 25° C. to about 30° C. for about 1 h to about 2 h. Water was added to the reaction mass under stirring. The reaction mass was concentrated and aq sodium bicarbonate solution was added to it, filtered and washed with water and dried at about 45° C. to about 50° C. in air dryer to obtain compound III. Yield: 4.55 g (78.17%).

Example 4

Preparation of Compound of Formula III

To a stirred solution of 6-[(2,4,6-trifluorobenzoyl) amino] pyridine-2-carboxylic acid (IV, 5 g) in dimethylformamide (25 ml), 1-ethyl-3-(3-dimethylaminopropyl) carbodiimide (EDC.HCl, 3.9 g), HOBT (2.7 g), N-methylmorpholine (2.6 g) and morpholine (1.8 g) were added. The reaction mass was stirred at about 25° C. to about 30° C. for about 4 hours to about 5 h. The progress of reaction was monitored using TLC/HPLC. Aqueous sodium carbonate solution was added to the reaction mass, stirred at about 25° C. to about 30° C. and filtered followed by water washing to obtain the compound III. Yield:4.8 g (78.14%).

Example 5

Preparation of Compound of N,N-dimethyl-6[(2,4,6-trifluorobenzoyl) amino]pyridine-2-carboxamide To a stirred solution of 6-[(2,4,6-trifluorobenzoyl)amino] pyridine-2-carboxylic acid (IV, 5 g) in dimethylformamide (50 ml), HATU (7.7 g), triethylamine (5.1 g) were added and stirred at about 25° C. to about 30° C. for about 20 min to about 30 min. Dimethylamine hydrochloride (1.7 g) was added to the reaction mass and stirred at about 25° C. to about 30° C. for about 2 h to about 3 h. The progress of reaction was monitored using TLC/HPLC. Aqueous sodium carbonate solution was added to the reaction mass, stirred at about 25° C. to about 30° C. and filtered followed by water washing to obtain N,N-dimethyl-6[(2,4,6-trifluorobenzoyl) amino]pyridine-2-carboxamide. Yield: 4.5 gm (78%)

$^1$H NMR (DMSO) δ (ppm): 2.92 (s, 3H), 2.99 (s, 3H), 7.34 (m, 3H) 8.0 (t, 1H) 8.2 (s, 1H).

Example 6

Preparation of 2,4,6-trifluoro-N[6-(pyrrolidin-1yl-carbonyl)pyridine-2-yl]benzamide To a stirred solution of 6-[(2,4,6-trifluorobenzoyl) amino] pyridine-2-carboxylic acid (IV, 20 g) in dimethylformamide (100 ml), HATU (30.8 g), DIPEA (10.5 g) were added and stirred at about 25° C. to about 30° C. for about 30 min. Pyrrolidone (6.2 g) was added to the reaction mass and stirred at about 25° C. to 30° C. for about 2 h to about 3 h. The progress of reaction was monitored using TLC/HPLC. After the completion of reaction, water and ethyl acetate were charged to the reaction mass and stirred at about 25° C. to about 30° C. The organic layer was separated, washed with sodium chloride solution and concentrated under vacuum at about 45° C. to obtain residue. The residue was charged in methanol, stirred at about 25° C. to about 30° C. for about 30 min to about 60 min and filtered to obtain 2,4,6-trifluoro-N[6-(pyrrolidin-1ylcarbonyl)pyridine-2-yl] benzamide. Yield: 5.0 g (81.43%)

Example 7

Preparation of Lasmiditan Hemisuccinate (IA)

To a stirred solution of compound III (50 g) in THF (500 ml), 1M solution of 1-methylpiperidine-4-yl-magnesium chloride in THF (616 ml) was added slowly at about –10° C. to about 0° C. under nitrogen atmosphere and stirred at about –10° C. to about 0° C. for about 1 h to about 2 h. The progress of reaction was monitored using TLC/HPLC. After the completion of reaction, water and ethyl acetate were added to the reaction mass, heated to about 20° C. to about 30° C. and stirred. The organic layer was separated, washed with sodium chloride solution, treated with charcoal, dried over sodium sulphate and solvent was distilled out completely. The residue was dissolved in IPA, succinic acid (16.16 g) was added to it and stirred at about 25° C. to about 30° C. for about 30 min to about 60 min. The reaction mass was heated to about 45° C. to about 50° C., stirred and filtered. The product was dried at about 40° C. to 45° C. in vacuum oven. HPLC Purity: 99.2%, Yield: 41 g (68.67%)

Mass spectrum: m/z=378(M+1); 1H NMR (DMSO) δ (ppm): 1.60 (t, 2H) 1.86 (d, 2H) 2.11 (s, 2H), 2.25 (s, 3H) 2.37 (s, 1H) 2.50 (t, 1H) 2.91 (d, 2H) 3.70 (d, 1H) 7.40 (t, 2H) 7.75 (d, 1H) 8.07 (t, 1H) 8.40 (d, 1H), 11.48 (s, 1H).

Example 8

Preparation of Lasmiditan Hemisuccinate (IA)

To a stirred solution of III (5 g) in THF, 1M solution of 1-methylpiperidine-4-yl-magnesium chloride in THF (65 ml) was added slowly at about –10° C. to 0° C. under nitrogen atmospher. The reaction mass was stirred at about –10° C. to about 0° C. for about 30 min to about 2 h. The progress of the reaction was monitored using TLC/HPLC. After the completion of reaction, THF was distilled out, water and MTBE were added to the reaction mass, heated to about 20° C. to about 30° C. The pH of the reaction mass was adjusted to about 8 to about 10 using dil. hydrochloric acid and stirred. The organic and aqueous layer were separated. The aqueous layer was extracted with MTBE. The combined organic layer was washed with sodium chloride solution and distilled out to obtain residue. The residue was dissolved in IPA, succinic acid (1.6 g) was charged and stirred at about 25° C. to about 30° C. for about 30 min to about 60 min. Reaction mass was heated at about 45° C. to 50° C. and maintained temperature for 30 min. The product was isolated by filtration and dried at about 40° C. to 45° C. in vacuum oven. Yield: 4.0 g (66%); HPLC Purity: 99.90%.

Example 9

Preparation of Lasmiditan Hemisuccinate (IA)

To a heterogeneous mass of magnesium (8.0 g) in THF, Iodine (0.05 g) and dibromoethane (5 ml) were charged under nitrogen atmosphere under stirring. The solution of N-methyl-4-chloro piperidine (21.9 g) in THF was added slowly to the reaction mass and stirred for about 30 min to obtain Grignard reagent.

The compound III (10 g) was charged in THF (100 ml) under nitrogen atmosphere and cooled to about –5° C. to about –10° C. Grignard reagent prepared above, was added drop-wise to the reaction mass and stirred about 30 min. The progress of reaction was monitored by TLC. After the completion of reaction, water and ethyl acetate were added to the reaction mass and stirred. The layers were separated. The aqueous layer was extracted with ethyl acetate. The combined organic layer was washed with sodium chloride solution, solvent was distilled out completely to obtain the residue. The residue was dissolved in IPA, succinic acid (3.23 g) was charged and stirred at about 25° C. to about 30° C. for about 30 min to about 60 min. Reaction mass was heated at about 45° C. to 50° C. and maintained temperature for 30 min. The product was isolated by filtration and dried at about 40° C. to 45° C. in vacuum oven. Yield: 5.2 g (43.55%).

Example 10

Preparation of Lasmiditan Hemisuccinate (IA)

Lasmiditan hemisuccinate (IA. 143 g) was dissolved in methanol (670 ml) at about 50° C. to about 60° C. The reaction mass was filtered through hyflo bed, washed with methanol. The filtrate was gradually cooled to about 20° C. to about 25° C., stirred for about 2 h to about 3 h, filtered, washed with methanol and dried at about 40° C. to 45° C. in vacuum dryer to obtain IA. Yield: 88 g (61%); HPLC Purity: 99.90% Impurity A: Not Detected.

| Pos [°2Θ] | d-spacing [Å] | Rel. Int [%] |
|---|---|---|
| 7.71 | 11.47 | 11.9 |
| 9.63 | 9.19 | 36.9 |
| 9.75 | 9.07 | 17.16 |
| 11.08 | 7.99 | 7.53 |
| 13.41 | 6.60 | 13.35 |
| 14.10 | 6.28 | 52.64 |
| 15.13 | 5.85 | 61.95 |
| 15.37 | 5.77 | 60.49 |
| 16.21 | 5.47 | 52.35 |
| 16.47 | 5.38 | 100 |
| 16.94 | 5.23 | 60.22 |
| 18.54 | 4.79 | 39.76 |
| 19.24 | 4.61 | 37.78 |
| 19.44 | 4.57 | 84.31 |
| 19.65 | 4.52 | 13.78 |
| 20.19 | 4.40 | 1.82 |
| 21.57 | 4.12 | 20.9 |
| 22.23 | 4.00 | 41.86 |
| 23.23 | 3.83 | 43.32 |
| 23.44 | 3.80 | 48.83 |
| 23.63 | 3.76 | 54.61 |
| 23.90 | 3.72 | 30.83 |
| 24.83 | 3.59 | 30.18 |
| 25.09 | 3.55 | 16.43 |
| 25.65 | 3.47 | 22.93 |
| 25.85 | 3.45 | 36.85 |
| 26.01 | 3.43 | 41.96 |
| 26.73 | 3.34 | 9.73 |
| 26.94 | 3.31 | 5.91 |
| 28.38 | 3.14 | 6.34 |
| 28.70 | 3.11 | 9.47 |
| 29.35 | 3.04 | 1.6 |
| 30.13 | 2.97 | 7.81 |
| 30.43 | 2.94 | 5.45 |
| 30.93 | 2.89 | 13.53 |
| 31.49 | 2.84 | 18.43 |
| 32.38 | 2.76 | 5.13 |
| 32.70 | 2.74 | 12.99 |
| 33.00 | 2.71 | 16.91 |
| 33.71 | 2.66 | 7.67 |
| 34.29 | 2.62 | 5.53 |
| 35.40 | 2.53 | 10.58 |
| 35.52 | 2.53 | 9.32 |
| 37.48 | 2.40 | 3.91 |
| 38.60 | 2.33 | 4.65 |
| 39.36 | 2.29 | 6.04 |
| 39.89 | 2.26 | 3.01 |
| 40.93 | 2.21 | 1.76 |
| 41.64 | 2.16 | 2.42 |
| 42.90 | 2.11 | 9.5 |

Example 11

Preparation of N-methoxy-N-methyl-6-{[(2,4,6-trifluorophenyl) carbonyl]amino}pyridine-2-carboxamide To a mixture of compound of formula IV (20 g) in dimethylformamide (125 ml), was added triethylamine (25.6 g), N,O-dimethylhydroxylamine hydrochloride (9.05 g) and HATU (38.5 g) and the reaction mixture was stirred at about 25° C. for about 15 h. Water, ethyl acetate and tetrahydrofuran were added to the reaction mixture and the two layers were separated. The aqueous layer was extracted with ethyl acetate and tetrahydrofuran. The combined organic layer was washed with aqueous sodium bicarbonate and aqueous sodium chloride solution. The organic layer was concentrated and the residue was crystallized in ethyl acetate. Yield: 21 g; HPLC Purity: 99.35%.

Example 12

Preparation of Compound of Formula I Lasmiditan Hemisuccinate

To a mixture of N-methoxy-N-methyl-6-{[(2,4,6-trifluorophenyl) carbonyl] amino}pyridine-2-carboxamide (18 g) in tetrahydrofuran (180 ml) cooled to about 0° C. to about −10° C., was added 1M solution of 1-methylpiperidine-4-yl-magnesium chloride in tetrahydrofuran (180 mL) slowly at about −5° C. to about −10° C. and the reaction mixture was stirred for about 1 h. Water was added slowly at about 0-5° C. and then ethyl acetate and the temperature was raised to about 25° C. The two layers were separated and the organic layer was washed with aqueous sodium chloride solution and concentrated. The residue was dissolved in isopropyl alcohol (180 mL) and succinic acid (6 g) was added to it at about 25° C. The reaction mixture was heated to about 50° C. The reaction mixture was cooled to about 20° C. The solid was filtered, washed with isopropyl alcohol and dried. Yield: 14.6 g; HPLC purity <98%. Impurity A=1%.

Example 13

Preparation of methyl-6-(2,4,6-trifluorobenzamido) pyridine carboxylate 2,4,6-trifluoro benzoic acid was added to dichloromethane and dimethyl formamide was added to the reaction mass. Oxalyl chloride was added to the reaction mass and the reaction mass was stirred at about 25° C. to 30° C. for about 30 to 40 minutes. The solvent was distilled off to get an oil. The obtained oil was dissolved in dichloromethane to obtain 2,4,6-trifluoro benzoyl chloride. Methyl-6-amino-pyridine-2-carboxylate was dissolved in dichloromethane and triethylamine was adde to the reaction mass. The reaction mass was then cooled to about 0° C. to 5° C. 2,4,6-trifluoro benzoyl chloride in dichloromethane was added to the reaction mass and reaction mass was stirred at about 0° C. to 5° C. for about 30 minutes. The temperature of the reaction mass was raised to about 25° C. 30° C. Aqueous hydrochloric acid was added to the reaction mass and reaction mass was stirred for about 10-15 min and organic and aqueous layer were separated. Organic layer was washed with saturated aqueous sodium bicarbonate and aqueous sodium chloride solution. The organic layer was distilled off to obtain a solid. The obtained solid was crystalized using methanol.

Example 13

Preparation of Compound of Formula IV

To a solution of sodium hydroxide (7.74 g) in water (150 mL), was added methyl-6-(2,4,6-trifluorobenzamido) pyridine-2-carboxylate (30 g) and tetrahydrofuran (300 mL) at about 25° C. and the reaction mixture was stirred for about 2 h. Aqueous hydrochloric acid and ethyl acetate were added to the reaction mixture and the two layers were separated. The organic layer was washed with aqueous sodium chloride solution. The organic layer was concentrated and the residue was crystallized in diisopropyl ether. Yield: 27.3 g; HPLC Purity: 98.14%

The invention claimed is:

1. A process for lasmiditan, a compound of formula I, or pharmaceutically acceptable salts thereof,

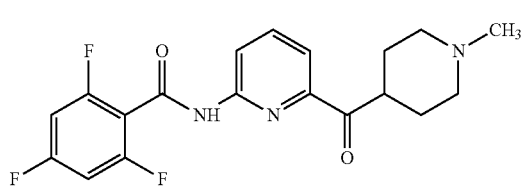

the process comprising:
(a) reacting a compound of formula III with a compound of formula IIA,

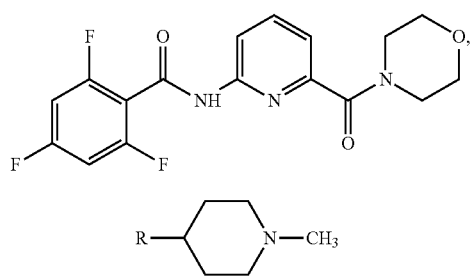

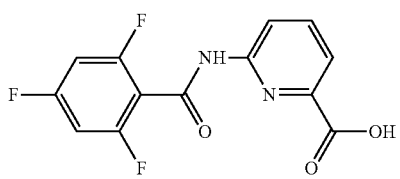

wherein R is MgX, Li, ZnX, or Sn (C$_1$-C$_6$ alkyl)$_3$; X is selected from the group consisting of Br, Cl, and I; to obtain lasmiditan, the compound of formula I; and
(b) optionally, converting lasmiditan, the compound of formula I, to a pharmaceutically acceptable salt.

2. The process of claim 1, wherein in step (b), lasmiditan is converted to lasmiditan hemisuccinate.

3. The process of claim 1, wherein the compound of formula III is prepared by a process comprising reacting a compound of formula IV,

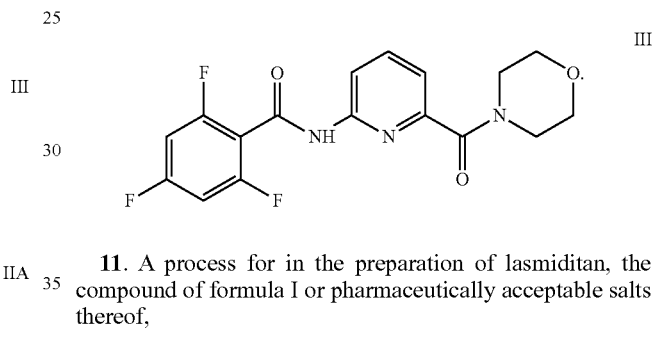

with morpholine to obtain the compound of formula III.

4. The process of claim 3, wherein the reaction of the compound of formula IV with morpholine is carried out in the presence of a coupling reagent.

5. The process of claim 4, wherein the coupling reagent is selected from the group consisting of a carbodiimide, a 1-hydroxybenzotriazole based or 1-hydroxy-7-azabenzotriazole based phosphonium and uronium salt, sulfinyl halide and phosphorus halide.

6. The process of claim 3, wherein the reaction of the compound of formula IV with morpholine is carried out in the presence of a base.

7. The process of claim 6, wherein the base is selected from the group consisting of an organic base, an inorganic base and mixture thereof.

8. The process of claim 7, wherein the organic base is selected from the group consisting of a trialkyl amine, a heterocyclic amine and an organilithium.

9. The process of claim 7, wherein the inorganic base is selected from the group consisting of a metal alkoxide, a metal carbonate, a metal bicarbonate, a metal hydroxide, wherein the metal is selected from the group consisting of sodium, potassium, lithium, calcium, cesium and magnesium.

10. A compound of formula III,

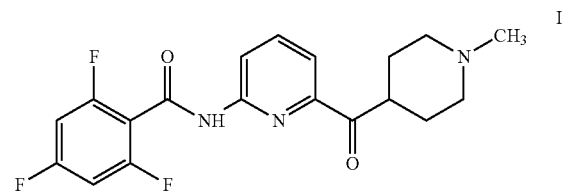 [SMILES: CN1CCC(C(=O)c2cccc(NC(=O)c3c(F)cc(F)cc3F)n2)CC1]

11. A process for in the preparation of lasmiditan, the compound of formula I or pharmaceutically acceptable salts thereof,

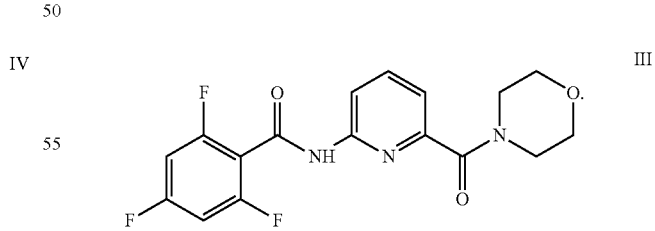

the process comprising converting the compound of formula III to lasmiditan,

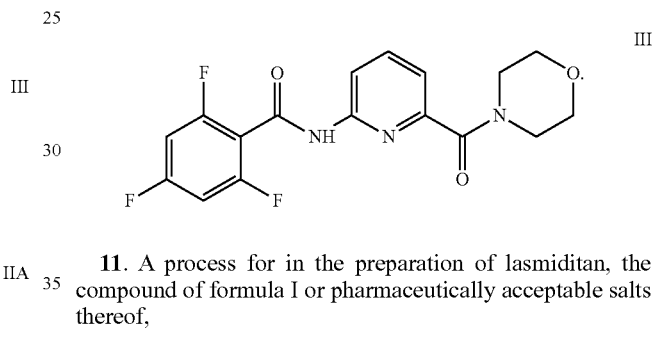

* * * * *